United States Patent [19]
Kawai et al.

[11] Patent Number: 6,056,404
[45] Date of Patent: May 2, 2000

[54] OPHTHALMIC APPARATUS

[75] Inventors: Noriji Kawai, Gamagori; Naoki Isogai, Nishio, both of Japan

[73] Assignee: Nidek Co., Ltd., Gamagori, Japan

[21] Appl. No.: 09/108,242

[22] Filed: Jul. 1, 1998

[30] Foreign Application Priority Data

Jul. 3, 1997 [JP] Japan ..... 9-194834
Apr. 10, 1998 [JP] Japan ..... 10-116188

[51] Int. Cl.⁷ ..... A61B 3/02
[52] U.S. Cl. ..... 351/237; 351/208; 351/211
[58] Field of Search ..... 351/200, 205, 351/201, 204, 208, 211, 221, 222, 237, 238, 245

[56] References Cited

U.S. PATENT DOCUMENTS

| | | |
|---|---|---|
| 5,463,430 | 10/1995 | Isogai et al. . |
| 5,561,482 | 10/1996 | Miyake . |
| 5,737,058 | 4/1998 | Umemura et al. . |
| 5,856,861 | 1/1999 | Hosoi et al. ............ 351/237 |

FOREIGN PATENT DOCUMENTS

| | | |
|---|---|---|
| 0 836 830 A1 | 4/1998 | European Pat. Off. . |
| 4-73046 | 3/1992 | Japan . |
| 6-46999 | 2/1994 | Japan . |
| 6-237897 | 8/1994 | Japan . |
| 7-213485 | 8/1995 | Japan . |
| 8-256983 | 10/1996 | Japan . |
| 8-256984 | 10/1996 | Japan . |
| 10-108836 | 4/1998 | Japan . |

*Primary Examiner*—George Manuel
*Attorney, Agent, or Firm*—Oliff & Berridge, PLC

[57] ABSTRACT

An ophthalmic apparatus for examining or measuring an eye to be examined, having an alignment optical system for aligning a position of the eye and that of a measuring system so as to be the predetermined positional relationship therebetween, the apparatus comprising a projecting device having a light source for projecting a pencil onto an examinee's face, a photo-receiving device which is an optical system having a positional detector for receiving reflex caused by the projecting device, the photo-receiving device having a detecting area which includes a right boundary of the examinee's face under the condition of being aligned with a right eye and a left boundary of the examinee's face under the condition of being aligned with a left eye, and a judging device for judging whether the eye is a right eye or a left eye in a manner of judging whether a face's boundary is the right boundary or the left boundary based on results detected by the photo-receiving device.

25 Claims, 8 Drawing Sheets

A ROTATING DIRECTION

OPHTHALMIC APPARATUS

BACKGROUND OF THE INVENTION

1. Field of the Invention

The present invention relates to an ophthalmic apparatus, and more particularly to the ophthalmic apparatus which examines or measures an eye to be examined, such as an apparatus for measuring an objective refractive power, an apparatus for measuring a corneal shape, and the like.

2. Description of Related Art

In conventional art, a setting-type ophthalmic apparatus is widely known as an apparatus for measuring an objective refractive power, and the like. The setting-type apparatus is configured so that an examining-measuring part can be moved relatively to a fixation base. When performing examination or measurement, an examiner moves the examining-measuring part relatively to the eye by operating a joystick or the like, thereby making the examining-measuring part be aligned with the eye one by one, causing the examination or measurement to be performed. Therefore, whether the eye is a right eye or a left eye can be known by detecting whether the examining-measuring part has moved to a right direction or a left direction with respect to the center of the fixation base.

On the other hand, in case of above mentioned setting-type ophthalmic apparatus, it is difficult to examine or measure each eye of an infancy, that of a lying patient, that of an animal and the like, further it is inconvenient to bring it to another place. Thus, a handheld-type ophthalmic apparatus has been proposed recently. The handheld-type ophthalmic apparatus does not has such function as to judge whether an eye to be examined is a right eye or a left eye based on a movement of an examining-measuring part though above mentioned setting-type apparatus has such function. In case of handheld-type, whether the examiner examines or measures a right eye or a left eye is recognized by inputting a data which indicates a right eye or a left eye with using a switch or the like.

However, it is complicated that an operation for inputting a data with using a switch in order to judge whether an eye to be examined is a right eye or a left eye. Further, the examiner sometimes forgets inputting a data, thereby resulting in a measurement error.

SUMMARY OF THE INVENTION

The present invention has been made in view of the above circumstances and has an object to overcome the above problems and to provide an ophthalmic apparatus for which an operation for inputting a data is not necessary in order to judge whether an eye to be examined is a right eye or a left eye, even though an examining-measuring part thereof does not move relatively to a fixation base.

Also, another object of the present invention is to provide a handheld-type ophthalmic apparatus by which an examiner can operate easily.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an ophthalmic apparatus of the present invention for examining or measuring an eye to be examined, having an alignment optical system for aligning a position of the eye and that of a measuring system so as to be the predetermined positional relationship therebetween, the apparatus comprises projecting means having a light source for projecting a pencil onto an examinee's face, photo-receiving means which is an optical system having a positional detector for receiving reflex caused by the projecting means, the photo-receiving means having a detecting area which includes a right boundary of the examinee's face under the condition of being aligned with a right eye and a left boundary of the examinee's face under the condition of being aligned with a left eye, and judging means for judging whether the eye is a right eye or a left eye in a manner of judging whether a face's boundary is the right boundary or the left boundary based on results detected by the photo-receiving means.

Another aspect of the ophthalmic apparatus of the present invention for examining or measuring an eye to be examined, having an alignment optical system for aligning a position of the eye and that of a measuring system so as to be the predetermined positional relationship therebetween, the apparatus comprises projecting means having a light source for projecting a pencil onto an examinee's face, photo-receiving means which is an optical system having a positional detector for receiving reflex caused by the projecting means, the photo-receiving means detecting positional relationship between a reflex-receiving part and a non-receiving part of the positional detector, and judging means for judging whether the eye is a right eye or a left eye based on results detected by the photo-receiving means.

According to the present invention, an operation for inputting a data is not necessary in order to judge whether the eye to be examined is a right eye or a left eye, even though the examining-measuring part thereof does not move relatively to the fixation base. Such ophthalmic apparatus is particularly suitable for a handheld-type.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

A detailed description of one preferred embodiment of an ophthalmic apparatus embodying the present invention will now be given referring to the accompanying drawings. In following description, an objective refractive power measurement apparatus is adopted as the preferred embodiment.

Figure 1:
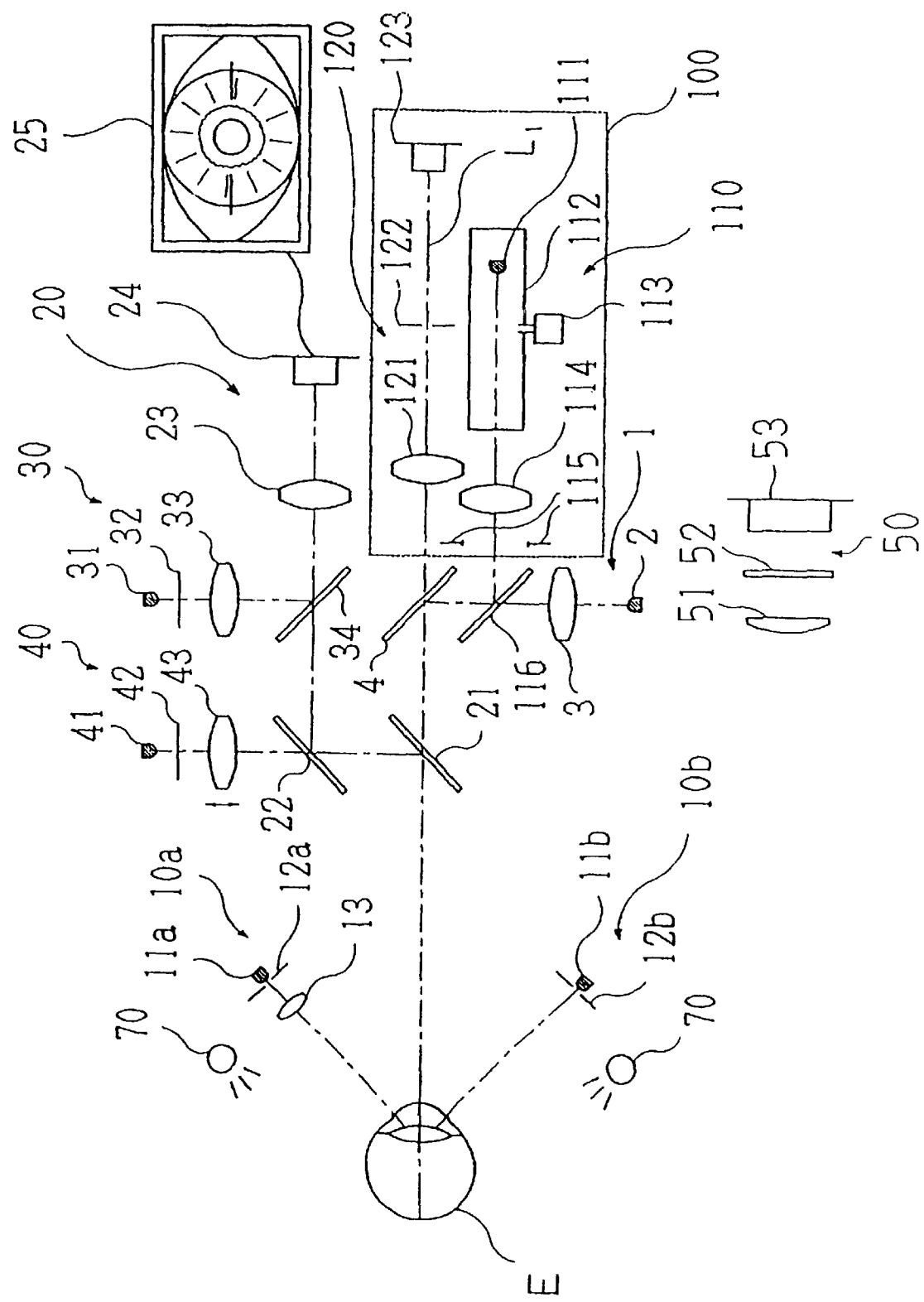
FIG. 1 is a side view showing a schematic arrangement of a part of an optical system of an apparatus according to the preferred embodiment of the present invention.

In FIG. 1, there is shown a side view of a schematic arrangement of a part of an optical system of the apparatus according to the preferred embodiment. The optical system consists of an alignment target-projecting optical system, a distance-target projecting optical system, a target detecting and observing optical system, a reticle projecting optical system, a fixation-target projecting optical system, a refractive power measuring optical system, a target-projecting optical system for judging whether an eye to be examined is a right eye or a left eye, a target-detecting optical system for judging whether the eye is a right eye or a left eye, and the like. Besides, in FIG. 1, the target-projecting optical system for judging whether the eye is a right eye or a left eye is not shown in convenience for drawing.

Herein, E is an eye to be examined. L1 is an optical axis for measurement of a measuring optical system mentioned below. Numeral 70 is a light source by which an anterior part of the eye E is illuminated. (Alignment target-projecting optical system)

Numeral 1 is an alignment target-projecting optical system. Light from a light source 2 for alignment is made to be approximately a parallel pencil by a collimating lens 3, then an axis thereof is made to coincide with the optical axis L1 for measurement by reflection of a beam splitter 4. Thereby, the pencil is projected onto the eye E from the front. (Distance-target projecting optical system)

Numerals 10a and 10b are distance-target projecting optical systems which project a target utilized for detecting a working distance between the eye E and the apparatus. The distance-target projecting optical system 10a consists of a light source 11a, a spot diaphragm 12a, and a collimating lens 13 which causes a light from a light source 11a to be approximately a parallel pencil. By such configuration, the system 10a projects the spot-diaphragm target onto the eye E from an optical infinite distance. On the contrary, the distance-target projecting optical system 10b consists of a light source 11b and a spot diaphragm 12b. By such configuration, the system 10b projects the spot-diaphragm target onto the eye E from an optical finite distance. The distance-target projecting optical systems 10a and 10b are disposed so that respective axes thereof can intersect with the optical axis L1 with making the same angles (In FIG. 1, the eye E is projected from upper and lower directions in convenience for drawing. However, it is preferable that the distance-target projecting optical systems 10a and 10b are disposed horizontally in order to prevent the pencil from being intercepted by an eyelash and an eyebrow).

To detect the working distance between the eye E and the apparatus is needed when precise alignment is performed in the direction of the working distance. However, the present invention has little relation to the detection, therefore, a description of method for detecting the working distance is omitted. Details are disclosed in Japanese Patent Laid-Open NO.HEI6-46999 corresponding to U.S. Pat. No. 5,463,430 entitled "EXAMINATION APPARATUS FOR EXAMINING AN OBJECT HAVING A SPHEROIDAL REFLECTIVE SURFACE".
(Target Detecting and Observing Optical System)

Numeral 20 is a target detecting and observing optical system. An image of an anterior part of the eye caused by the light source 70, a corneal reflex caused by the alignment target-projecting optical system 1, and corneal reflexes caused by the distance-target projecting optical systems 10a and 10b are reflected by dichloic mirrors 21 and 22, forming images on a photographing element of a camera 24 for observation by an image forming lens 23. In the preferred embodiment, a CCD camera for near infrared range is adopted as the camera 24. The image of the anterior part of the eye and corneal reflexes photographed by the camera 24 are displayed on a TV monitor 25.
(Reticle Projecting Optical System)

Figure 2:
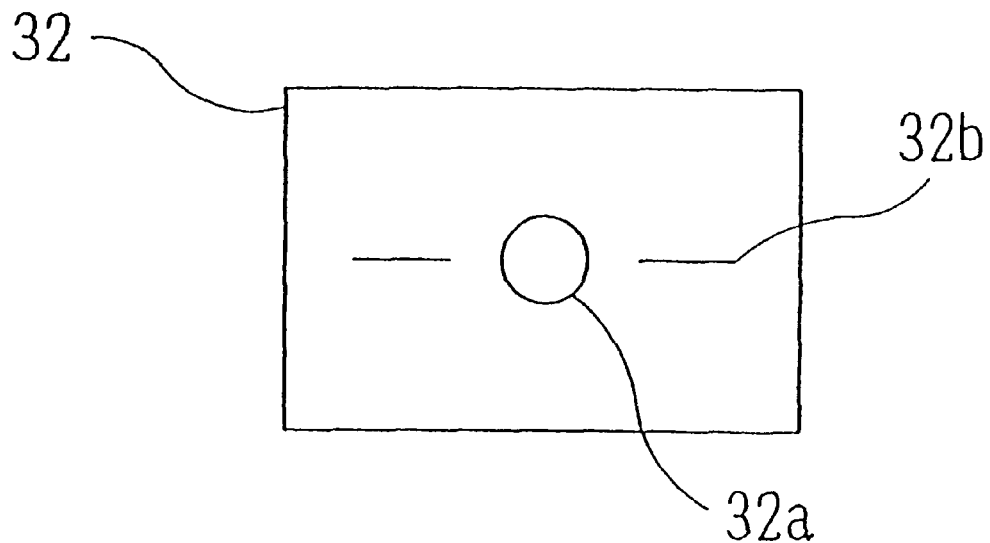
FIG. 2 is a view for illustrating a reticle mark provided for a reticle plate.

Numeral 30 is a reticle projecting optical system. Light from the light source 31 via a reticle plate 32 passes through a projecting lens 33, being reflected by a beam splitter 34, then forming an image on the photographing element of the camera 24 by the image forming lens 23. As shown in FIG. 2, a reticle mark is formed on the reticle plate 32. The image of the reticle mark photographed by the camera 24 is displayed on the TV monitor 25. The reticle marks are classified into two types, one is a circular reticle mark 32a, and the other is a line mark 32b of which a cylinder axis of a measuring system indicates a direction of 0°. Alternatively, the line mark 32b may not necessary for the apparatus. On the contrary, the line mark indicating a direction of 90° may be additionally provided thereon.
(Fixation-Target Projecting Optical System)

Numeral 40 is a fixation-target projecting optical system. The fixation-target projecting optical system 40 is made to coincide with the target detecting and observing optical system 20 by above mentioned dichloic mirror 22. A light source 41 illuminates a fixation target 42 from which a pencil passes through a projecting lens 43 and the dichloic mirror 22. After that, the pencil is reflected by the dichloic mirror 21, being transmitted to the eye E, thereby the eye E being fixed to the fixation target 42. The projecting lens 43 fogs the eye E by moving in the direction of the optical axis.
(Refractive Power Measuring Optical System)

Numeral 100 is a refractive power measuring optical system. The refractive power measuring optical system 100 consists of a slit projecting optical system and a slit-image detecting optical system.

Figure 3:
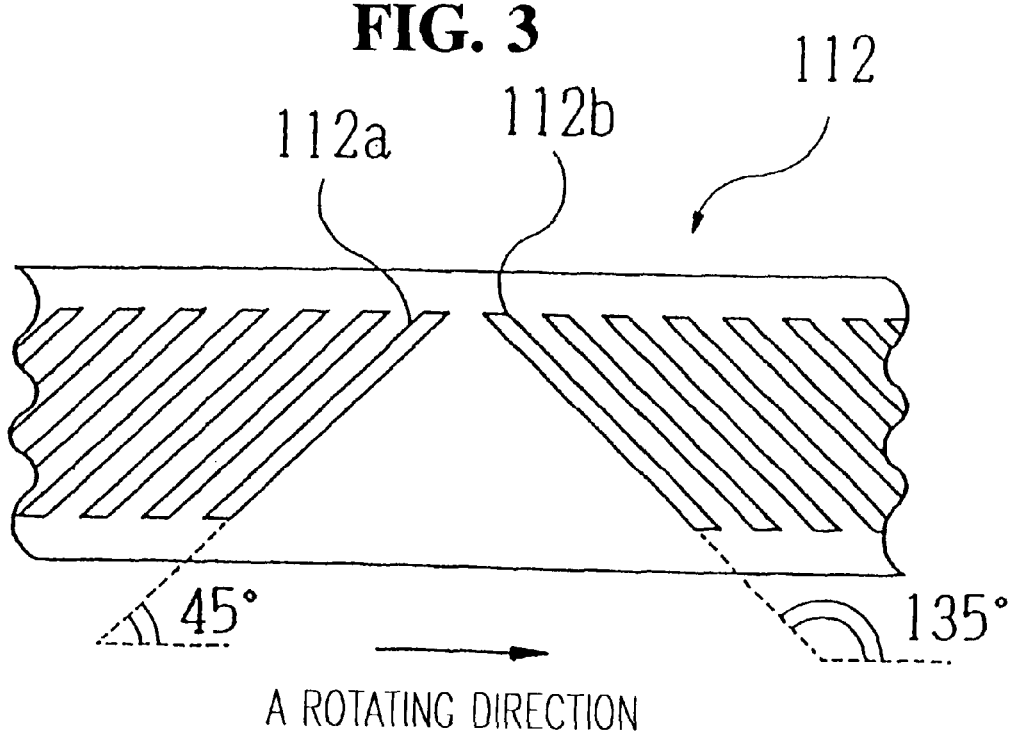
FIG. 3 is a developed view showing a slit aperture provided for a side face of a rotation sector.

Numeral 110 is a slit projecting optical system. Light from the light source 111 illuminates a slit aperture 112a or 112b provided for a cylindrical rotation sector 112 which rotates with a fixed velocity to a fixed direction by a motor 113. On the side face of the rotation sector 112, as shown in FIG. 3, a plurality of slit apertures 112a and 112b which have two kinds of different angles of inclination respectively are provided. The slit aperture 112a is disposed so as to have an angle 45° of inclination to a rotating direction of the rotation sector 112. The slit aperture 112b is disposed so as to have an angle 135° of inclination to a rotating direction so as to intersect at right angles with the slit aperture 112a. The slit pencil scanned by the rotation sector 112 passes through the projecting lens 114 by which the light source 111 is made to be conjugate with a position close to a cornea of the eye E.

After that, the slit pencil is limited by a limit diaphragm 115, then being made to coincide with the axis of the alignment target-projecting optical system 1 by reflection of the beam splitter 116 and transmitted to the eye E, then converging at the position close to the cornea of the eye E, thus being projected onto a fundus of the eye E. Besides, since the rotation sector 112 has slit apertures having different angles, a sensor which is not shown is provided thereon in order to detect which slit pencil is projected.

Figure 4:
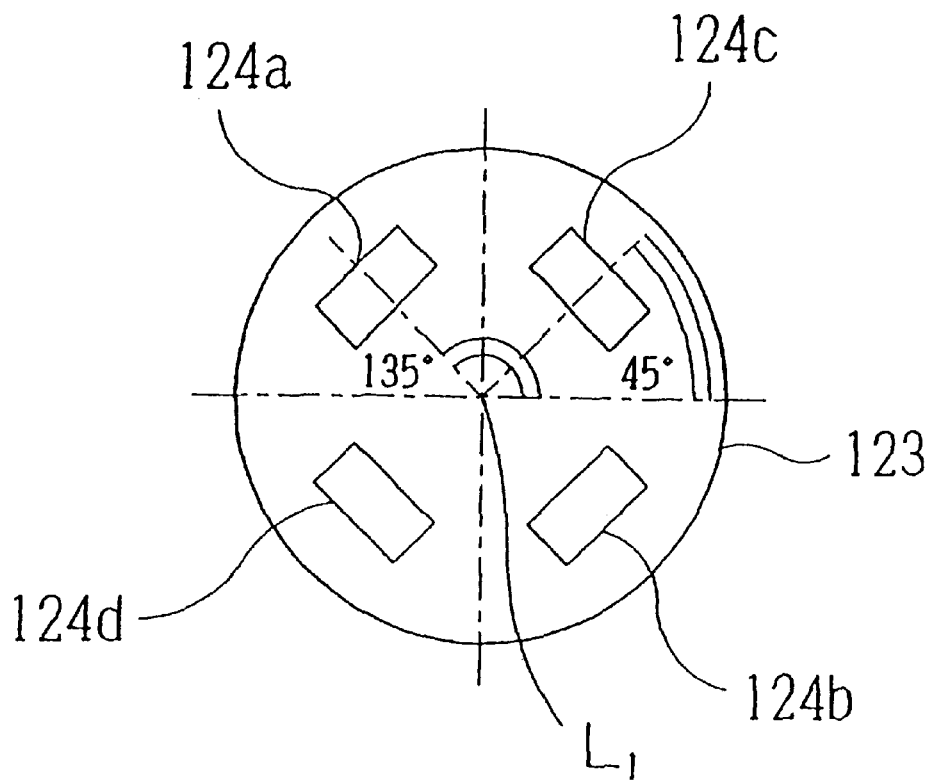
FIG. 4 is a view for illustrating an arrangement of four photo-detectors of photo-detecting part.

Numeral 120 is a slit image detecting optical system which includes a photo-receiving lens 121, a diaphragm 122 and a photo-detecting part 123 on the optical axis L1. The diaphragm 122 is disposed at the back focal point of the photo-receiving lens 121, and the photo-detecting part 123 is disposed at approximately conjugate position relative to the cornea of the eye E with respect to the photo-receiving lens 121. The photo-detecting part 123 is provided with four photo-detectors 124a–124d on the surface thereof as shown in FIG. 4. The photo-detectors 124a and 124b are disposed so as to be symmetric with the center at the optical axis L1, in the same way, the photo-detectors 124c and 124d are disposed so as to be symmetric with the center at the optical axis L1. These two pairs of photo-detectors are respectively made to correspond to a scanning direction of a slit pencil on the fundus of the eye E which is projected by the slit apertures 112a and 112b having two kinds of angles of inclination (the slit pencil on the fundus comes to be scanned in a direction intersecting with a long direction of the slit at right angles, as it were). By such configuration, the two pairs of photo-detectors detect the slit pencil reflected by the fundus of the eye E. In the preferred embodiment, under the condition that the slit pencil by the slit apertures 112a is scanned on the fundus of the eye E having hyperopia or myopia exclusive of astigmatism, a pair of photo-detectors 124a and 124b are disposed so as to correspond to a direction intersecting at right angles with a long direction of the slit so as to receive a pencil with the photo-detecting part 123. In the same way, under the condition that the slit pencil by the slit apertures 122b is scanned, a pair of photo-detectors 124c and 124d are disposed so as to correspond to a direction intersecting at right angles with a long direction of the slit so as to receive a pencil with the photo-detecting part 123.

The photo-detectors 124a and 124b are disposed so as to correspond to a direction intersecting at right angles with a long direction of the slit in case that a slit pencil in a certain direction is projected onto the eye E. A corneal center or a center of a visual axis of the eye E is detected based on an output signal of a phase difference from the photo-detectors 124c and 124d thereat. Based on the detected corneal center or the detected center of the visual axis and respective output signals from the photo-detectors 124a and 124b disposed so as to correspond to above-mentioned certain direction, each refractive power at each corneal position corresponding to each photo-detector is calculated. Thereby, a refractive power in a meridian direction with respect to the corneal center or the center of the visual axis is calculated, and existence of irregular astigmatism is detected. In addition, a detailed description concerning a measurement for refractive power of an eye is disclosed by Japanese Patent Laid-Open No.HEI10-108836 corresponding to U.S. patent application Ser. No. 08/942,633 and European Patent Publication EP0836830A1 entitled "OPHTHALMIC MEASUREMENT APPARATUS".

(Target-Detecting Optical System for Judging Whether the Eye is a Right Eye or a Left Eye)

Numeral 50 is a target-detecting optical system for judging whether the eye is a right eye or a left eye. Reflex from the examinee, s face, caused by a pencil projected by below-mentioned target-projecting optical system for judging whether the eye is a right eye or a left eye, forms an image on a positional detector 53 by an image forming lens 51 of wide-angle lens. At the time, by providing therein a filter 52 which transmits near infrared-ray and intercepts visible-ray and the like, an excess disturbance light such as a sun light, an illumination light of a room or the like can be eliminated. In addition, a PSD is utilized for the positional detector 53 in the preferred embodiment. Since a detecting speed of a PSD is high, contrast of light flickering with high speed can be detected. Further, if DC component of a light component detected by a PSD is cut, then only a light component of the flickering light source can be extracted. That is, if the light source of below-mentioned target-projecting optical system for judging whether the eye is a right eye or a left eye is made to be flickering with high speed, then a light component of near infrared-ray such as sun light or the like which has passed through the filter 52 can be eliminated, resulting in that only a light component of reflex, caused by the light source of target-projecting optical system for judging whether the eye is a right eye or a left eye, can be extracted. In addition, the image forming lens 51, the filter 52 and the positional detector 53 are disposed below with respect to the optical axis L1.

Figure 5:
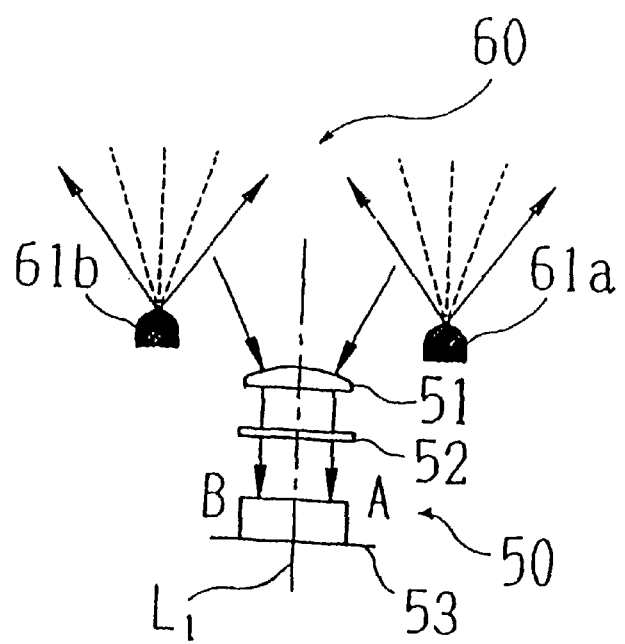
FIG. 5 is a top view showing a schematic arrangement of a part of an optical system of an apparatus according to the preferred embodiment of the present invention.

FIG. 5 is a top view showing a schematic arrangement of a part of an optical system of the apparatus according to the preferred embodiment. Besides, the target-detecting optical system and the target-projecting optical system both for judging whether the eye is a right eye or a left eye are only shown in convenience for drawing, thus other optical systems are not shown.

(Target-Projecting Optical System for Judging Whether the Eye is a right Eye or a Left Eye)

Numerals 60 is a target-projecting optical system for judging whether the eye is a right eye or a left eye. A light source 61a which projects light onto the examinee's face is disposed at a right side of the apparatus from the examiners sight, and a light source 61b is disposed at a left side from the examiner's sight. Thus, the light sources 61a and 61b are symmetric about the optical axis L1. Further, the light sources 61a and 61b are disposed so as to illuminate a relative large area of the examinee's face, when the apparatus is aligned with the eye E. Further, the light sources 61a and 61b are configured so as to flicker with high speed controlled by a controller which is not shown (flickering is allowed to be only once or more).

In addition, since LEDs are adopted as the light sources 2, 11a, 11b, 31, 61a, 61b, 70 and 111 which emit pencil, within a range of near infrared-ray, a pencil can be projected without troubling the eye E with a burden. In addition, if a filter which transmits near infrared-ray and intercepts visible-ray or the like is disposed between the dichloic mirror 22 and the beam splitter 34, then the camera 24 may not restricted to that for use in near infrared-ray. Also, the light source 31 utilized for the reticle projecting optical system 30 is allowed to be a normal light source which emits a visible-ray.

Next, the operation of the ophthalmic apparatus having above mentioned architecture will be described below.

Firstly, the apparatus is made to be moved in front of the eye E, then the light sources 70, 2 and 31 are made to be emitted by using switches not shown, or the like. Image of an anterior part of the eye E caused by the light source 70, a corneal reflex formed on the eye E caused by the alignment target-projecting optical system 1 and an image of the reticle mark caused by the reticle projecting optical system 30 are photographed by the camera 24, then being displayed on the TV monitor 25 (LCD display). The examiner causes the apparatus to move so that the corneal reflex caused by the light source 2 can be positioned at the center of the reticle mark 32a with observing the image of the corneal reflex and the image of the reticle mark displayed on the TV monitor 25, thus causing an alignment to be performed in vertical and lateral directions. In addition, in case that the line mark 32b is provided, the examiner adjusts an inclination of the apparatus with observing the TV monitor 25 so that the image of the line mark 32b may be horizontal. Further, the examiner adjusts a working distance roughly by bringing the corneal reflex of the eye E into focus.

When it is confirmed that the corneal reflex detected by using an image processing technique is in a predetermined area and that a rough alignment of the eye E in lateral and vertical directions and a rough alignment of a working distance are completed, then the controller causes the light sources 61a and 61b to flicker with high speed (flickering is allowed to be only once or more. In addition, the light sources 61a and 61b may be emitted not only after completing a rough alignment but also at regular intervals of time). The pencils from the light sources 61a and 61b illuminate the examinee's face. A part of reflex thereof passes through the image forming lens 51 and the filter 52, then being received by the positional detector 53 (see FIG. 6).

Herein, a PSD is such that a ratio of electric current from both edges is defined by a position of the center of gravity of incidence onto a receiving-surface. If each amount of the electric current from both edges is detected and the ratio is calculated, then the position of the center of gravity of received-light (reflex) can be known. Then, the position of the center of gravity is compared with the center of a PSD (the positional detector 53). If the position of the center of gravity of received-light (reflex) is closer to A side than the center of the PSD, then the eye is judged a left eye. If the position of the center of gravity of received-light (reflex) is closer to B side than the center of the PSD, then the eye is judged a right eye. In case of FIG. 6, the eye E is judged a right eye.

Figure 6:
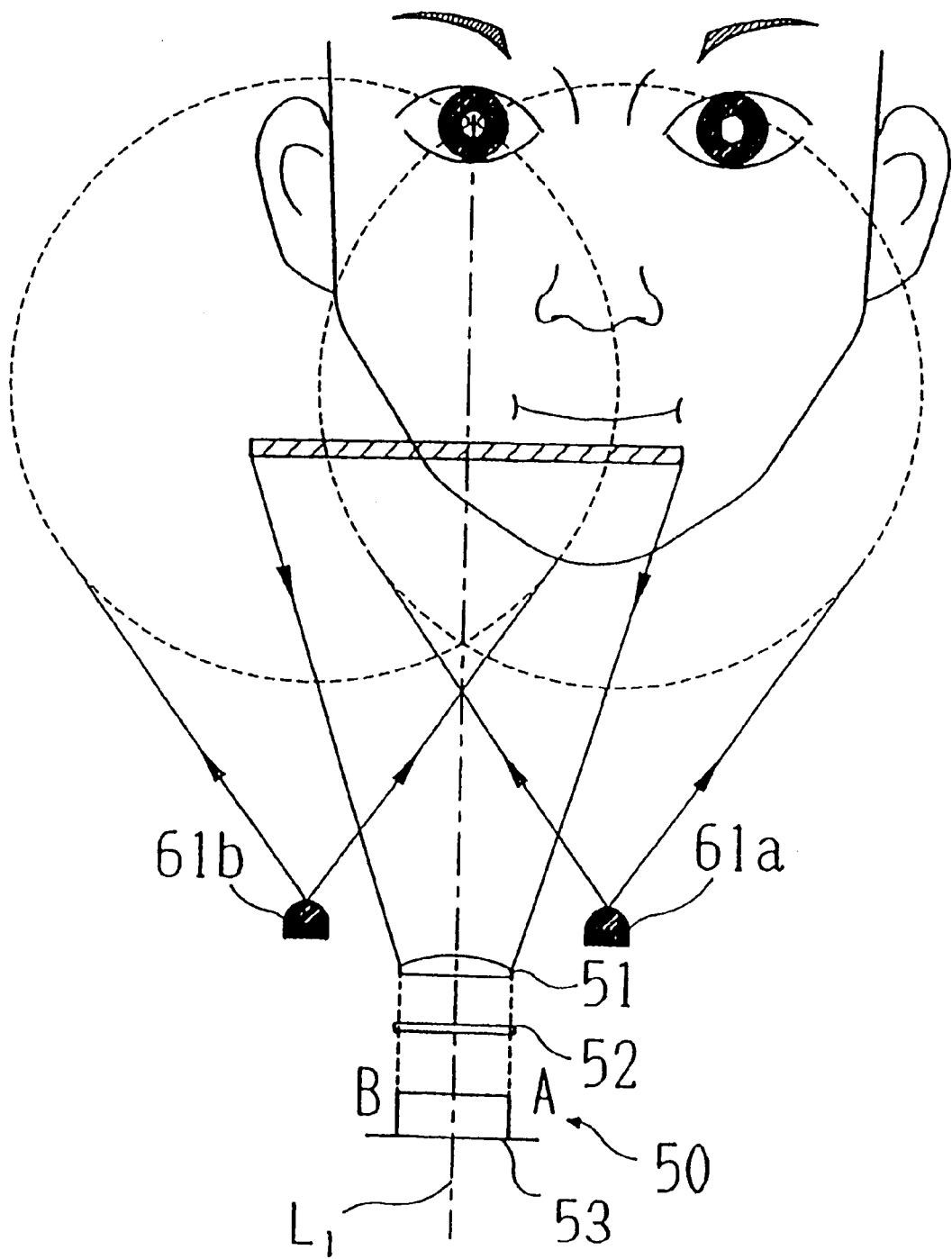
FIG. 6 is a view for illustrating a projection of light onto an examinee's face, a range illuminated by light and a mechanism for receiving reflex thereof.
Figure 7:
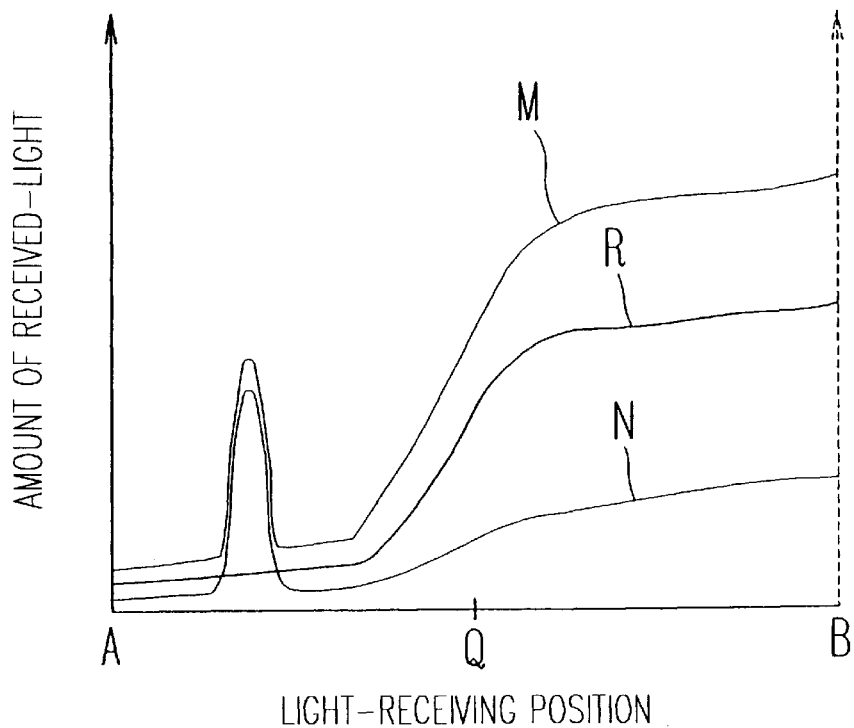
FIG. 7 is a view for illustrating an amount of received-light (reflex) and a light-receiving position which are detected by a positional detector.
Figure 8:
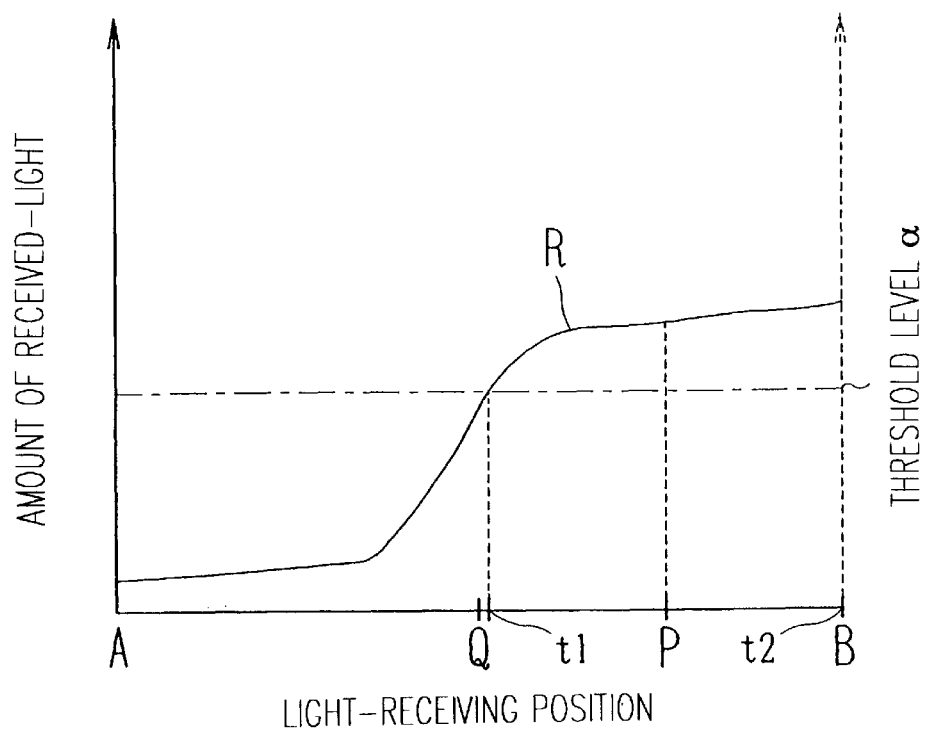
FIG. 8 is a view for illustrating an amount of received-light (reflex) and a light-receiving position which are detected by a CCD, and a threshold operation.
Figure 9:
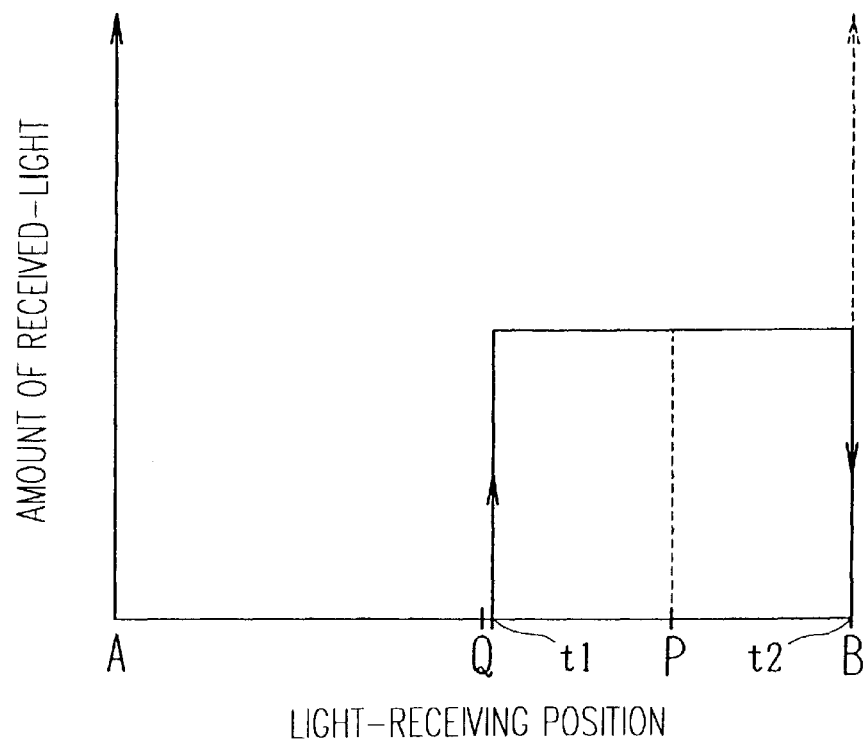
FIG. 9 is a view for illustrating condition after processing an amount of received-light (reflex) by a threshold operation.
Figure 10:
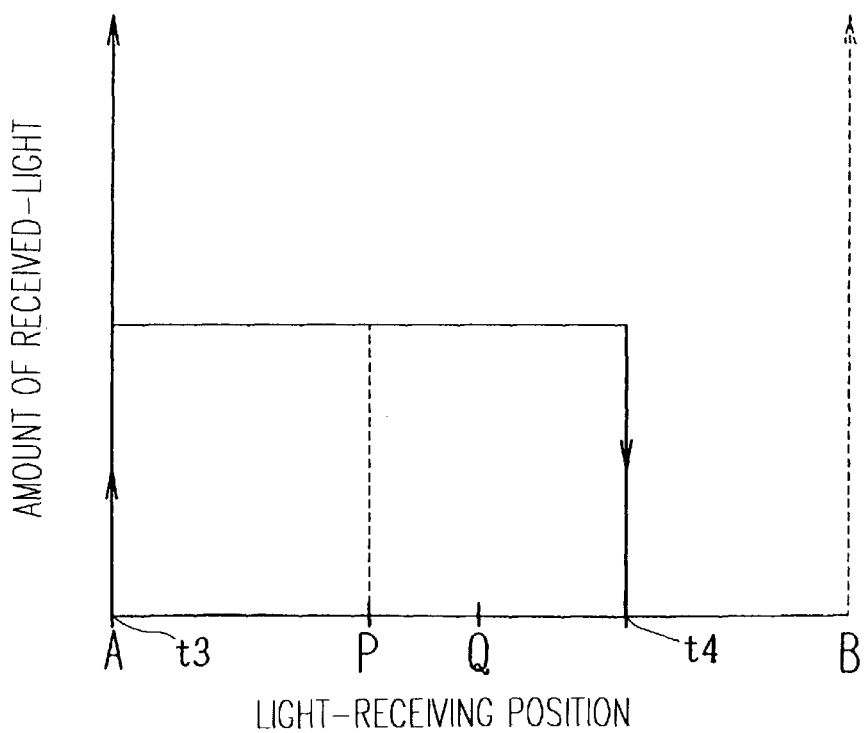
FIG. 10 is a view for illustrating condition after processing an amount of received-light (reflex) by a threshold operation.

As the positional detector 53, an one-dimensional CCD may be used instead of a PSD. As shown in FIG. 6, if the light from the light sources 61a and 61b illuminates the examinee's face, then a part of reflex from the face forms an image on the positional detector 53 by the image forming lens 51 and the filter 52. In case of FIG. 6, namely in case of a right eye, relationship between an amount of light (reflex) received by the positional detector 53 and a light-receiving position is as shown in FIG. 7. A graph M shows the relationship therebetween in a case that the light sources 61a and 61b are turned on, and a graph N shows the relationship therebetween in a case that the light sources 61a and 61b are turned off. Thus, if N is subtracted from M, then only a graph R being component of reflex caused by the light sources 61a and 61b can be extracted. In case of the one-dimensional CCD, as shown in FIG. 8, a central position P between a point t1 and a point t2 can be calculated by processing an amount of light (reflex) received by the positional detector 53 (the one-dimensional CCD) by a threshold operation. A predetermined value may be defined as the threshold level α, and may be stored in advance. Alternatively, one-half of a peak value of amount of received-light (reflex) may be defined as the threshold level α. After calculating the central position P, as the same way of using a PSD, it can be judged whether the eye E is a right eye or a left eye by detecting whether the central position P is closer to A side or B side with respect to a central position Q of the positional detector 53 (the one-dimensional CCD). In addition, it is not necessary to calculate the central position of received-light (reflex), namely, it is allowed as far as the central position may be utilized for obtaining a balance of an amount of received-light (reflex). The balance of an amount of light (reflex) can be calculated based on a rising edge position and/or a falling edge position of received-light (reflex) which are found by a threshold operation. Thereby, it can be judged whether the eye E is a right eye or a left eye. FIG. 9 shows relationship between a light-receiving position and an amount of received-light (reflex) after processing an amount of received-light (reflex) shown in FIG. 8 by a threshold level α. As shown in FIG. 9, since a falling edge position t2 is at a position B (only a rising edge position t1 is in A–B), the eye E is judged a right eye. In addition, in case that relationship between a light-receiving position and an amount of received-light (reflex) after processing an amount of received-light (reflex) becomes as shown in FIG. 10, since a rising edge position t3 is at a position A (only a falling edge position t4 is in A–B), the eye E is judged a left eye. In case that both a rising edge position and a falling edge position are in A–B, whether the eye is a right eye or a left eye can be judged based on a central position between the rising edge position and the falling edge position.

Further, if a two-dimensional CCD is adopted as the positional detector 53, then an area where reflex is received is made to be enlarged, thus allowing detection in plurality of horizontal lines. Thereby, it is judged more precisely whether the eye is a right eye or a left eye.

In addition, if detected image is digitized, being stored into an image memory and analyzed, thereby a position of the center of gravity of an amount of received-light (reflex) can be calculated.

Figure 11:
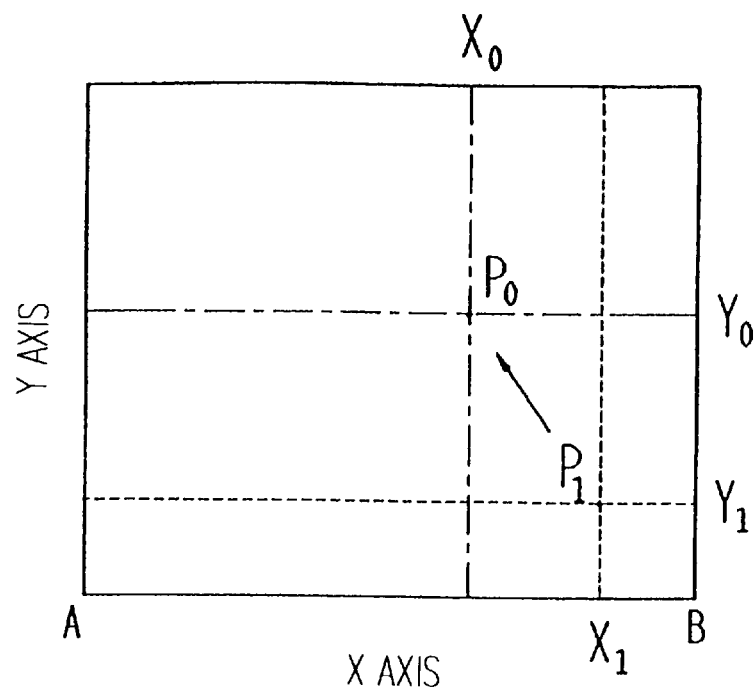
FIG. 11 is a view for illustrating detection of an alignment deviation made by a two-dimensional CCD.

In case that the positional detector 53 is a two-dimensional CCD, as shown in FIG. 11, if coordinates (X0, Y0) is made to be stored in advance, then an alignment deviation can be detected roughly based on an amount of deviation and a deviating direction between coordinates (X1, Y1) and coordinates (X0, Y0). Where, coordinates (X0, Y0) denotes a position P0 being the center of gravity (a central position) of an amount of received-light (reflex) when the optical axis L1 is aligned with the eye E exactly, and coordinates (X1, Y1) denotes a position P1 being the center of gravity (a central position) of an amount of received-light (reflex) which is detected. Then, if an arrow post or the like is displayed on the TV monitor 25 based on the amount of deviation and the deviating direction which are detected, then the examiner can perform alignment in accordance with. In case that the positional detector 53 is an one-dimensional CCD or a PSD, an alignment deviation in only one direction (X direction) can be detected.

By processing an amount of light (reflex) received by the positional detector 53 by another threshold operation, further information can be obtained.

Figure 12A:
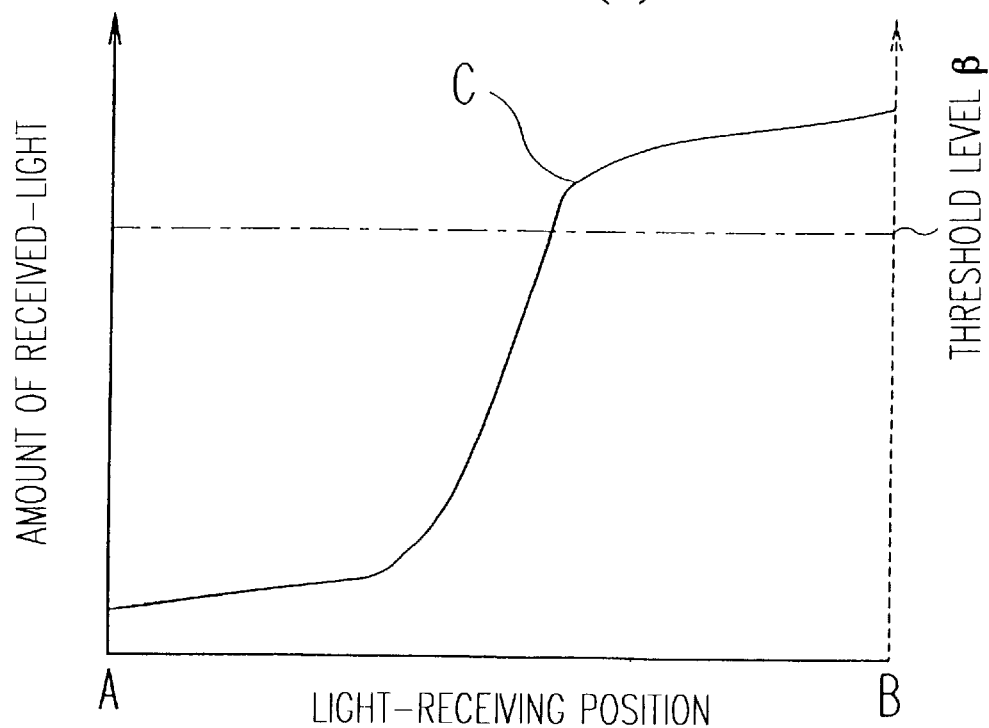
FIGS. 12(a)–12(c) are views for illustrating each threshold operation in case that each threshold level is set as β, δ and γ respectively in order to detect a distance between the examinee and the apparatus.

As shown in FIG. 12(a), if a certain threshold level β is set with respect to an amount of light (reflex) received by the positional detector 53, then a warning can be made so that a distance between the examinee and the apparatus may not be closer than the required distance. In case that an amount of light (reflex) from the examinee's face, received by the positional detector 53, is greater than a required amount, namely in case that it is greater than the predetermined threshold level β as denoted by a graph C, the warning is made continuously by a voice sound or a display on the TV monitor 25 until an amount of received-light (reflex) is less than the predetermined threshold level β.

Figure 12B:
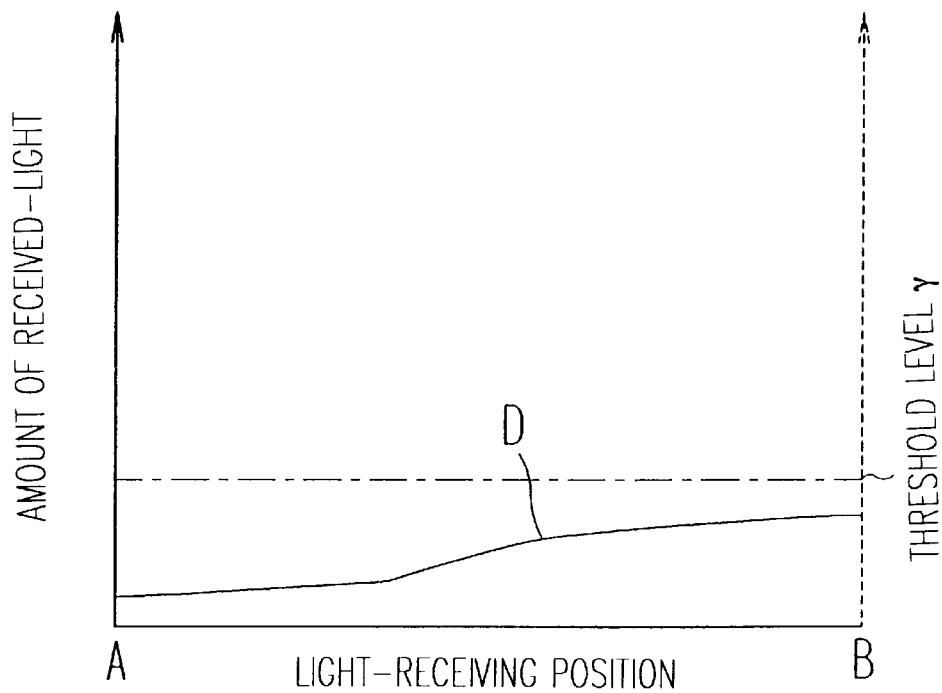

In addition, as shown in FIG. 12(b), if a certain threshold level γ is set with respect to an amount of light (reflex) received by said positional detector 53, then a warning can be made so that a distance between the examinee and the apparatus may not be further than the required distance. In case that an amount of light (reflex) from the examinee's face, received by the positional detector 53, is less than a required amount, namely in case that it is less than the predetermined threshold level γ as denoted by a graph D, the warning is made continuously by a voice sound or a display on the TV monitor 25 until an amount of received-light (reflex) is greater than the predetermined threshold level γ.

Figure 12C:
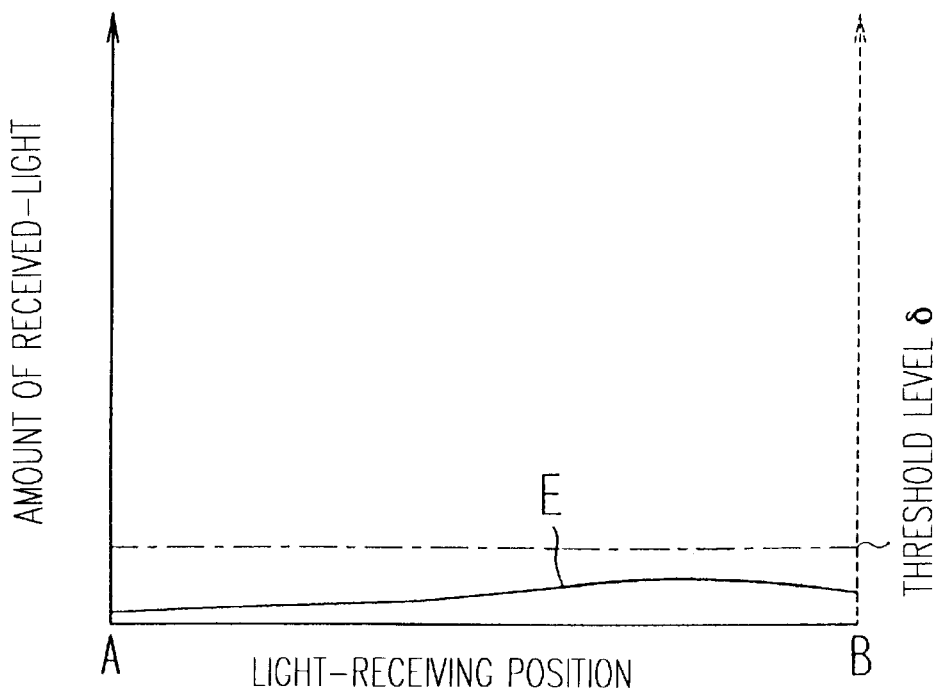

In case that the apparatus moves automatically relative to the eye to perform a positional adjustment, the operation can be stopped or restarted on the basis of above mentioned information. In addition, in case of the apparatus such as tonometer or the like, which performs measurement by being closer toward the eye, when the apparatus being too close thereto, the operation can be automatically stopped by using an electromagnetic brake and the like based on above mentioned information Further, as shown in FIG. 12(c), if a certain threshold level δ is set with respect to an amount of light (reflex) received by said positional detector 53, then it can be detected whether the examinee's face is in front of the apparatus or not. In this case, if an amount of light (reflex) from the examinee's face, received by the positional detector 53, is less than the predetermined threshold level δ as denoted by a graph E, it is judged that the examinee's face does not exist in front of the apparatus. Then, various kind of operation is made to be stopped. On the contrary, if an amount of received-light (reflex) is greater than the predetermined threshold level δ, then various kind of operation such as a precise alignment detection, a display on the TV monitor and the like are made to be started. The operation of the apparatus can be controlled in accordance with an amount of light (reflex) received by the positional detector 53. Accordingly, power saving can be achieved, further, the apparatus becomes easy to use. In addition, the threshold levels γ and δ may be same values. Actually, a time component may be added as a parameter. In this case, the apparatus may be preferably configured so as to wait till a set time has passed after that an amount of received-light (reflex) becomes greater or less than the threshold level δ, successively, to stop or to restart the operation. Thereby, malfunction can be decreased.

In addition, a well known method can be utilized for performing an alignment with the eye in lateral, vertical and working distance directions exclusive of the above mentioned method utilized by the preferred embodiment.

The present invention is not restricted to the apparatus for measuring an only one eye. Namely, the present invention can be utilized for the apparatus provided with a measuring system for both eyes. Further, in the preferred embodiment, the target-projecting optical system 60 for judging whether the eye is a right eye or a left eye is configured so as to have two light sources (the light sources 61a and 61b), thereby projecting light from both sides of the optical axis L1, however, the configuration may not restricted to this type. Namely, the light source may be only one. In other words, such apparatus may be allowed that illuminates the examinee's face from any directions as far as a relative large area of the examinee's face can be illuminated. Further, a target-detecting optical system 50 for judging whether the eye is a right eye or a left eye may not necessarily be disposed at a position perpendicular to the optical axis L1. In addition, various kinds of methods can be utilized for judging whether the eye is a right eye or a left eye. For example, it can be done on the basis of a part (a darkness part) where does not reflect light from the target-projecting optical system 60 for judging whether the eye is a right eye or a left eye.

Further, the present invention is not restricted to only the hand-held type ophthalmic apparatus, but it is also utilized for the setting-type ophthalmic apparatus.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus for examining or measuring an eye to be examined, having an alignment optical system for aligning a position of the eye and that of a measuring system so as to be the predetermined positional relationship therebetween, the apparatus comprising:

projecting means having a light source for projecting a pencil onto an examinee's face;

photo-receiving means which is an optical system having a positional detector for receiving reflex caused by said projecting means, said photo-receiving means having a detecting area which includes a right boundary of the examinee's face under the condition of being aligned with a right eye and a left boundary of the examinee's face under the condition of being aligned with a left eye; and judging means for judging whether the eye is a right eye or a left eye in a manner of judging whether a face's boundary is the right boundary or the left boundary based on results detected by said photo-receiving means.

2. The ophthalmic apparatus according to claim 1, wherein said projecting means is disposed so as to be symmetric about a measuring axis of said measuring system or a visual axis of the eye.

3. The ophthalmic apparatus according to claim 1, wherein said positional detector is disposed below a measuring axis of said measuring system or a visual axis of the eye.

4. The ophthalmic apparatus according to claim 1, wherein the pencil projected by said projecting means has a wavelength within a range of near infrared-ray; and said photo-receiving means has wavelength-selecting means for transmitting near infrared-ray and intercepting light exclusive of light having wavelength within a range of near infrared-ray.

5. The ophthalmic apparatus according to claim 1, wherein said judging means has comparing means for comparing detected-results of reflex upon turning off said light source with detected-results of reflex upon turning on the same.

6. The ophthalmic apparatus according to claim 1, wherein said positional detector is a CCD; and said judging means comprising:

setting means for setting a predetermined threshold level with respect to an amount of received-light; and calculating means for calculating a central position of received-light or a balance of an amount of light based on the threshold level set by said setting means and results detected by said CCD.

7. The ophthalmic apparatus according to claim 6, wherein said calculating means calculates the central position of received-light or a balance of an amount of light based on a rising edge position and/or a falling edge position of received-light.

8. The ophthalmic apparatus according to claim 6, further comprising:

storing means for storing a mean central position of received-light at the time when said measuring system is aligned with the eye;

calculating means for calculating an alignment deviation between the eye and said measuring system based on coordinates of the central position stored by said storing means and coordinates of the central position of received-light detected by said CCD; and displaying means for displaying the alignment deviation calculated by said calculating means.

9. The ophthalmic apparatus according to claim 1, further comprising:

setting means for setting a predetermined threshold level with respect to an amount of received-light;

detecting means for detecting relationship of distance between the examinee and the apparatus based on said threshold level and an amount of received-light; and warning means for warning an examiner based on results detected by said detecting means.

10. The ophthalmic apparatus according to claim 1, further comprising:

setting means for setting a predetermined threshold level with respect to an amount of received-light;

detecting means for detecting existence of the examinee's face or relationship of distance between the examinee and the apparatus based on said threshold level and an amount of received-light; and controlling means for controlling operation of the apparatus based on results detected by said detecting means.

11. The ophthalmic apparatus according to claim 1, the apparatus comprises a case of a hand-held type.

12. An ophthalmic apparatus for examining or measuring an eye to be examined, having an alignment optical system for aligning a position of the eye and that of a measuring system so as to be the predetermined positional relationship therebetween, the apparatus comprising:

projecting means having a light source for projecting a pencil onto an examinee's face;

photo-receiving means which is an optical system having a positional detector for receiving reflex caused by said projecting means, said photo-receiving means detecting positional relationship between a reflex-receiving part and a non-receiving part of said positional detector; and judging means for judging whether the eye is a right eye or a left eye based on results detected by said photo-receiving means.

13. The ophthalmic apparatus according to claim 12, wherein said projecting means is disposed so as to be symmetric about a measuring axis of said measuring system or a visual axis of the eye.

14. The ophthalmic apparatus according to claim 12, wherein said positional detector is disposed below a measuring axis of said measuring system or a visual axis of the eye.

15. The ophthalmic apparatus according to claim 12, wherein the pencil projected by said projecting means has a wavelength within a range of near infrared-ray; and said photo-receiving means has wavelength-selecting means for transmitting near infrared-ray and intercepting light exclusive of light having wavelength within a range of near infrared-ray.

16. The ophthalmic apparatus according to claim 12, wherein said positional detector is a PSD; and said judging means judges whether the eye is a right eye or a left eye in a manner of calculating a position of the center of gravity of reflex caused by said projecting means based on results detected by said PSD.

17. The ophthalmic apparatus according to claim 16, further comprising:

storing means for storing a mean position of the center of gravity of reflex at the time when said measuring system is aligned with the eye;

calculating means for calculating an alignment deviation between the eye and said measuring system based on coordinates of the position of the center of gravity stored by said storing means and coordinates of the position of the center of gravity of reflex detected by said PSD; and displaying means for displaying the alignment deviation calculated by said calculating means.

18. The ophthalmic apparatus according to claim 16, further comprising:

flash-controlling means for flickering said light source; and extracting means for extracting only a light component of said light source which is flickering based on results detected by said PSD.

19. The ophthalmic apparatus according to claim 12, wherein said positional detector is a CCD; and said judging means comprising:

setting means for setting a predetermined threshold level with respect to an amount of received-light; and calculating means for calculating a central position of received-light or a balance of an amount of light based on the threshold level set by said setting means and results detected by said CCD.

20. The ophthalmic apparatus according to claim 19, wherein said calculating means calculates the central position of received-light or a balance of an amount of light based on a rising edge position and/or a falling edge position of received-light.

21. The ophthalmic apparatus according to claim 19, further comprising:

storing means for storing a mean central position of received-light at the time when said measuring system is aligned with the eye;

calculating means for calculating an alignment deviation between the eye and said measuring system based on coordinates of the central position stored by said storing means and coordinates of the central position of received-light detected by said CCD; and displaying means for displaying the alignment deviation calculated by said calculating means.

22. The ophthalmic apparatus according to claim 19, wherein said judging means has comparing means for comparing a detected-results of reflex upon turning off said light source with a detected result of reflex upon turning on the same.

23. The ophthalmic apparatus according to claim 12, further comprising:

setting means for setting a predetermined threshold level with respect to an amount of received-light;

detecting means for detecting relationship of distance between the examinee and the apparatus based on said threshold level and an amount of received-light; and warning means for warning an examiner based on results detected by said detecting means.

24. The ophthalmic apparatus according to claim 12, further comprising:

setting means for setting a predetermined threshold level with respect to an amount of received-light;

detecting means for detecting existence of the examinee's face or relationship of distance between the examinee and the apparatus based on said threshold level and an amount of received-light; and controlling means for controlling an operation of the apparatus based on results detected by said detecting means.

25. The ophthalmic apparatus according to claim 12, the apparatus comprises a case of a hand-held type.

* * * * *